United States Patent [19]

Nilsson et al.

[11] Patent Number: 4,476,875
[45] Date of Patent: Oct. 16, 1984

[54] METHOD AND APPARATUS FOR MEASURING FLOW MOTIONS IN A FLUID

[76] Inventors: Gert E. Nilsson, Fräsaregatan 9, 582 66 Linköping; Jan T. Tenland, Konsistoriegatan 10B, 582 34 Linköping; Per A. Öberg, Ugglebovägen 79, 590 60 Ljungsbro, all of Sweden

[21] Appl. No.: 87,685

[22] Filed: Oct. 23, 1979

[30] Foreign Application Priority Data

Oct. 31, 1978 [SE] Sweden ............... 7811288

[51] Int. Cl.³ ............................................. A61B 5/02
[52] U.S. Cl. .................................. 128/666; 128/691
[58] Field of Search .............................. 128/665–667, 128/691, 631, 634

[56] References Cited

U.S. PATENT DOCUMENTS

| | | | |
|---|---|---|---|
| 3,511,227 | 5/1970 | Johnson | 128/666 |
| 3,822,695 | 7/1974 | Takayama | 128/634 |
| 4,109,647 | 8/1978 | Stern et al. | 128/666 |

FOREIGN PATENT DOCUMENTS

| | | | |
|---|---|---|---|
| 1202612 | 8/1970 | United Kingdom | 128/665 |
| 1407023 | 9/1975 | United Kingdom | 73/861 |

OTHER PUBLICATIONS

Stern, M. D., "In vivo Evaluation of Microcirculation by Coherent Light Scattering" *Nature*, vol. 254, Mar. 1975, pp. 56–58.

Watkins, D. et al., "An Instrument to Measure Cutaneous Blood Flow Using the Doppler Shift of Laser Light," *IEEE Trans. Biomed Engrg*, vol. BME-25, No. 1, Jan. 1978, pp. 28–33.

Stern, M. D. et al., "Measurement of Local Tissue Blood Flow by Laser Doppler Spectroscopy", Abstract, Proc. of Federation of Amer. Societies for Exper. Biology, 60th Ann. Meeting, Anaheim, Cal., Apr. 1976.

*Primary Examiner*—Kyle L. Howell
*Assistant Examiner*—Francis J. Jaworski
*Attorney, Agent, or Firm*—Browdy and Neimark

[57] ABSTRACT

For determining flow motions in a fluid containing light scattering particles, in particular for determining the blood circulation in the superficial blood vessels in a tissue, a section of the fluid is illuminated with monochromatic light from a laser (1). Light scattered from particles in the fluid and from any surrounding stationary structures is gathered from two, at least partially separated but mutually adjacent regions of the illuminated section of the fluid and transmitted separately to two separate photodetectors (5, 5'). From the output signal of each photodetector a signal is derived, which contains the beat frequency components resulting from interference between light components received by the photodetector, which have different frequencies due to the Doppler frequency shift of the light scattered by moving particles. The two signals so derived from the output signals of the two photodetectors are subtracted from each other and the signal resulting from this subtraction is used as a measure of flow motions in the fluid.

12 Claims, 7 Drawing Figures

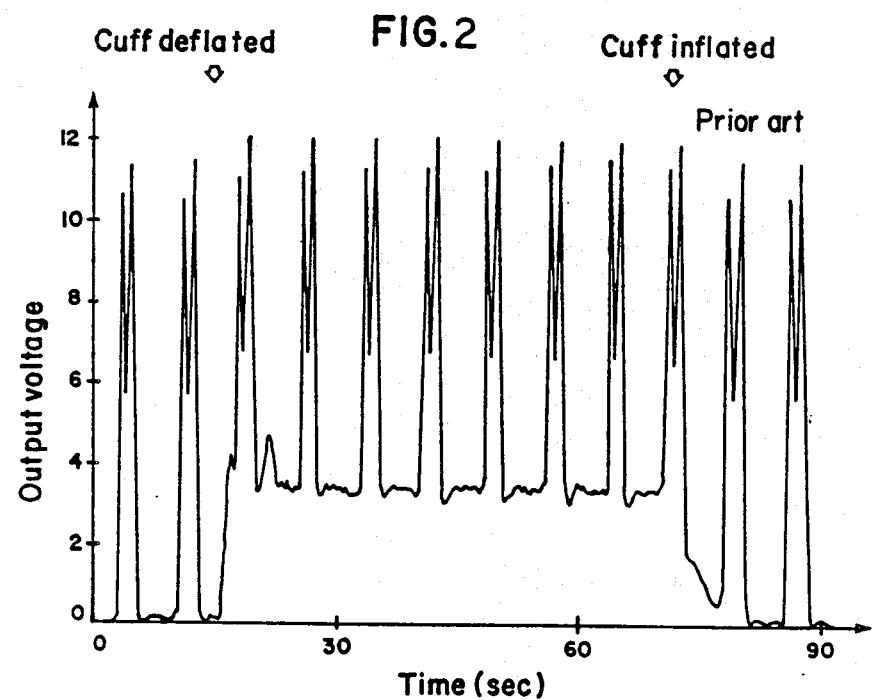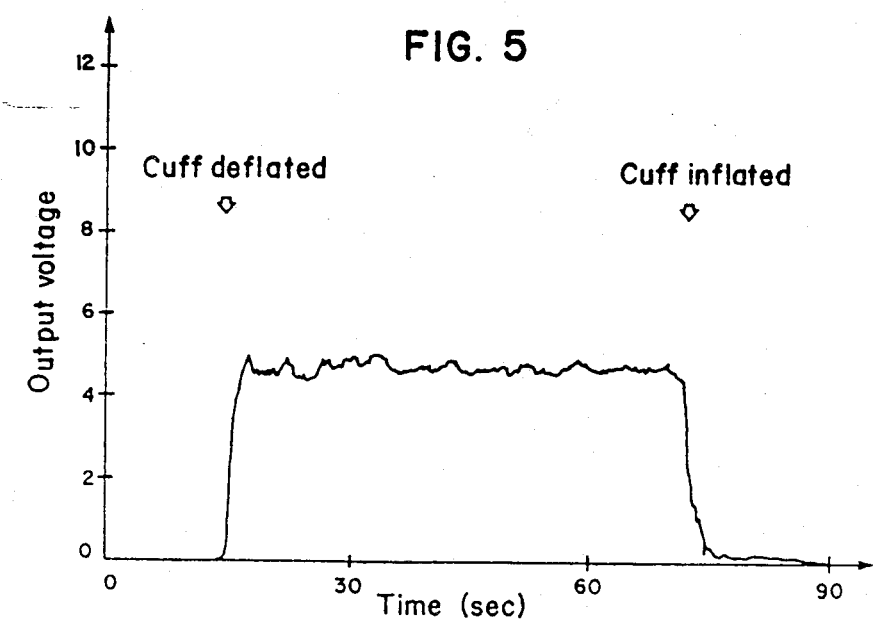

METHOD AND APPARATUS FOR MEASURING FLOW MOTIONS IN A FLUID

The present invention is related to a method and an apparatus for detecting or measuring flow motions in a fluid containing light scattering particles, in particular for studying and measuring the blood flow in the superficial blood vessels in a tissue. The fluid is illuminated with monochromatic light from a laser and light scattered from the particles in the fluid is analyzed with respect to its content of light components having a frequency deviating from the frequency of the irradiating light, which components originate from moving particles in the fluid, and the presence of such components is used as a measure of the flow motion of the fluid.

This measuring technique is known i.a. from D. Watkins and G. A. Holloway "An instrument to measure cutaneous blood flow using the Doppler shift of laser light", IEEE Trans. Biomed. Eng. Vol. BME-25, No. 1, January 1978, and from M. D. Stern "In vivo evaluation of microcirculation by coherent light scattering", Nature, Vol. 254, March 1975, and also from M. D. Stern and D. L. Lappe, "Measurement of local tissue blood flow by laser Doppler Spectroscopy", Fed. Proc, Vol. 35, No. 3, 1976. These previously described measuring methods are used for measuring the blood circulation in a tissue. One serious problem in connection with this prior art technique is caused by mode interference in the laser cavity, which produces intermittent, high amplitude, noiselike signals occurring within the frequency range under study. These disturbances, which are due to temperature related phenomena in the laser cavity, prevent a continuous measurement of the blood flow.

For eliminating this serious disadvantage one has attempted to use a temperature stabilized single-mode laser. This type of laser has been tested with a certain success, but the low power output (0.2 mW) of this laser has severely restricted the usability of the method with regard to its sensitivity and resolution. One has also contemplated the use of a high power laser of the etalon type, but his has been rejected due to the large size and high costs of this type of laser.

The object of the present invention is therefore to provide an improved method and a corresponding improved apparatus of the kind mentioned initially, which provides a very substantial reduction of the adverse effects caused by mode interference and also by wide-band beam amplitude noise so that a continuous measurement with the utilization of a low-cost multi-mode laser as a light source is made possible.

According to the invention this is achieved in that light scattered by particles in the fluid and by any adjacent stationary structures is gathered from two, at least partially separated but mutually adjacent regions of the illuminated section of the fluid and conveyed to two separate photodetectors, whereby these two photodetectors receive light scattered at least partially by different particles. From the output signal of each photodetector a signal is derived, which represents the beat frequency components between light components of different frequencies received by the photodetectors, and the two signals derived from the output signals of the two photodetectors are subsequently subtracted from each other and the resulting signal from this signal subtraction is used as a measure of the flow motions in the fluid.

In a preferred embodiment of the invention the output signal of each photodetector is subjected to a high-pass filtering and is subsequently normalized by being divided by the total output signal of the photodetector. The resulting signal of the signal subtraction is preferably subjected to a band-pass filtering and is thereafter squared. The filtered and squared signal is subsequently subtracted from a signal adjusted to correspond to the signal value in the absence of flow motions in the fluid and is then averaged.

As according to the invention two photodetectors are used, which both receive light reflected from the illuminated section of the fluid and any adjacent substantially stationary structures and the output signals from these two photodetectors are subtracted, perturbations caused by mode interference in the laser beam as well as by wide-band beam amplitude noise are rejected very effectively from the differential signal resulting from the signal subtraction. Also other disturbances are suppressed, such as 60 Hz intensity variations in the ambient light, and also to a certain extent disturbances due to movement artefacts when measuring the blood circulation in superficial blood vessels. One might believe that the subtraction of the output signals from the two photodetectors would also result in a suppression of the useful desired signal components, i.e. the beat frequency components between frequency-shifted light scattered from the moving particles and unshifted light. This will not be the case, however, since according to the invention the two photodetectors receive scattered light originating at least partially from different particles in the fluid. It can be shown that the movements of different particles in the fluid constitute statistically mutually independent realisations of the same stochastic process, wherefore the random fashion in which the movable particles move through the illuminated section of the fluid gives cause to randomly fluctuating phase shifts of the beat frequency components in the output signals from the two photodetectors. Consequently, the subtraction of these two signals results in an aggregation of the flow related beat frequency components, whereby the desired useful signal is amplified. In this way the invention results in a substantially improved signal-to-noise ratio besides the fact that the adverse effects of mode interference in the laser beam are suppressed to a negligible level.

Although the invention has been developed and in the following will be described in connection with a method and an apparatus for determining the blood flow in the superficial blood vessels in a tissue, it can be used also in other connections for determining or measuring the flow motions in a fluid containing light scattering particles.

In the following the invention will be described in more detail with reference to the accompanying drawings, wherein:

FIG. 2 shows a graphic recording of the blood flow in the finger tip of a person made with the use of an apparatus according to FIG. 1;

FIG. 5 shows a graphic recording corresponding to the one in FIG. 2 but made with the use of the apparatus according to FIGS. 3 and 4;

Figure 7:
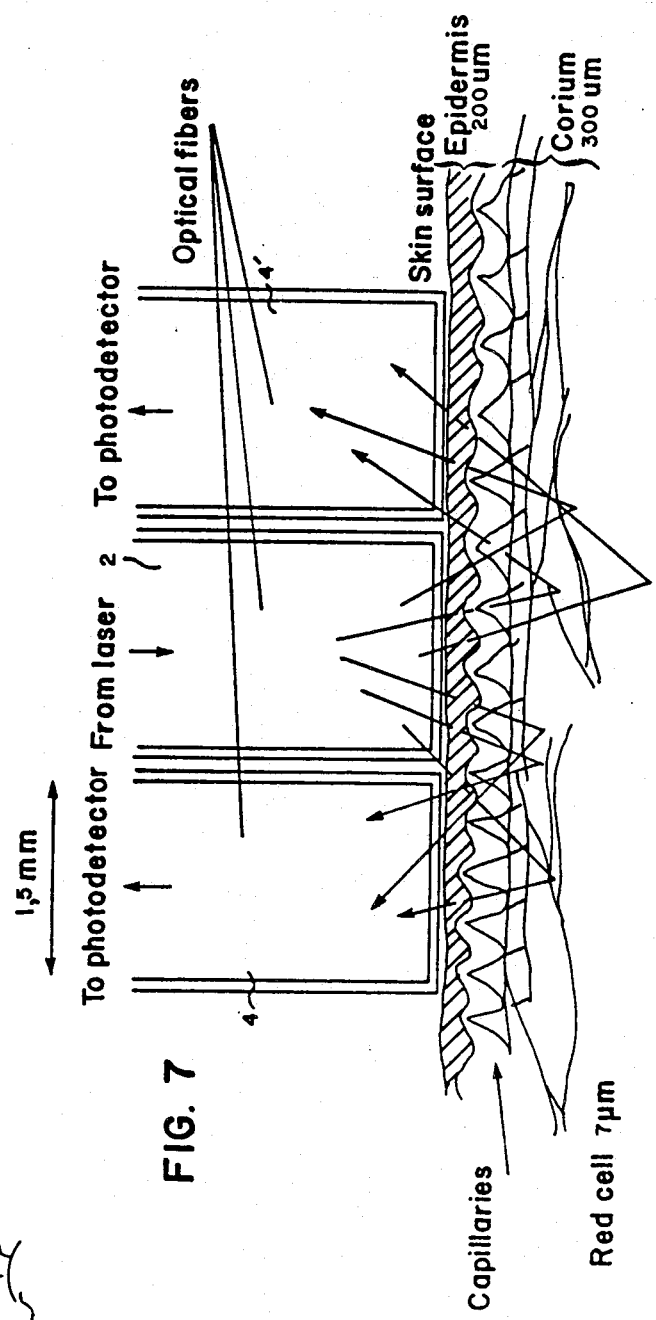
Figure 6:
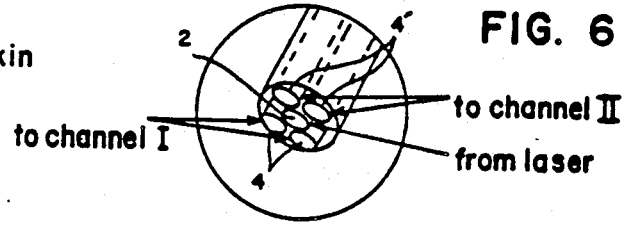

FIG. 6 illustrated schematically a possible arrangement of the optical fibres in an apparatus according to the invention; and FIG. 7 illustrates schematically the application of the measuring probe on the skin surface, in section and at a substantially enlarged scale.

Figure 1:
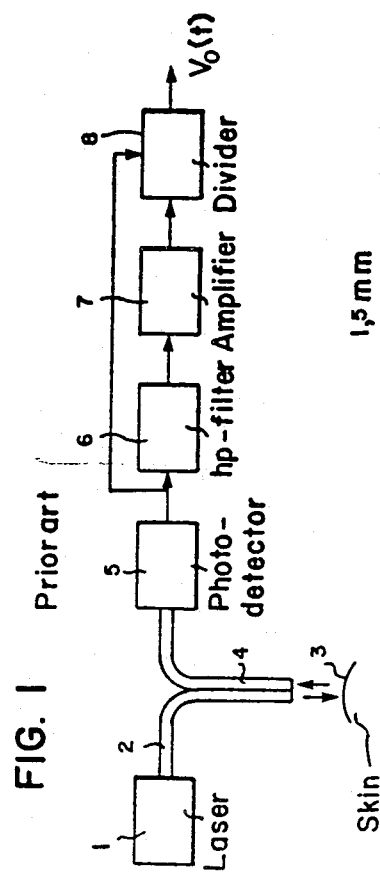
FIG. 1 is a block diagram of a prior art apparatus for measuring the blood circulation in a biologic tissue.

FIG. 1 shows a schematic block diagram for a prior art apparatus for measuring blood flow in the capillary layer of a biologic tissue, for instance the finger tip of a person. Monochromatic light from a laser 1 is transmitted through an optical fibre 2 and directed towards the skin surface 3. The light penetrates the skin and the tissue to a depth of approximately 1 mm and scattered light, partly from the surrounding tissue and partly from the blood cells in the capillary network, is gathered and transmitted by means of an optical fibre 4 to a photodetector 5. Scattered light from the moving blood cells displays a frequency shift due to the Doppler effect and on the photo sensitive surface of the photodetector this frequency-shifted light will interfere with unshifted light. Consequently, the output signal from the photodetector will contain a large number of beat frequencies, primarily within the frequency range 0-20 kHz. The wideband output signal from the photo detector is high-pass filtered in a high-pass filter 6 so that the dc component is removed. The remaining ac component of the signal is amplified in a low-noise linear amplifier 7 and subsequently normalized in a divider 8. The normalization of the signal is made by dividing the output signal from the amplifier 7 by the total output signal from the photodetector, whereby the output signal from the divider 8 will become independent (at least to a certain extent) of intensity variations in the laser light. The normalized signal is processed and provides after band-pass filtering and averaging a signal with the shape illustrated in the diagram in FIG. 2. This diagram shows the output voltage as a function of time when using the prior art apparatus according to FIG. 1 for determining the blood circulation in the fingertip of a person. The blood circulation in the arm of the patient was interrupted by means of an inflated cuff round the upper part of the arm. The cuff was deflated at the instant indicated in the diagram and re-inflated after an interval of about 60 seconds, as indicated in the diagram. As can be seen from the diagram the output signal of this prior art apparatus contains very large peak-disturbances which appear periodically in the signal and have an amplitude several times larger than the amplitude of the useful, blood flow related signal. These high-amplitude perturbations in the signal originate from mode interference in the laser cavity and preclude a continuous measurement of the blood flow for the duration of these perturbations. This high amplitude noise is present for approximately 50% of the total measuring period. The clinical use of this measuring method is entirely dependent on the possibility of reducing these high-amplitude disturbances to an acceptable level.

Figure 3:
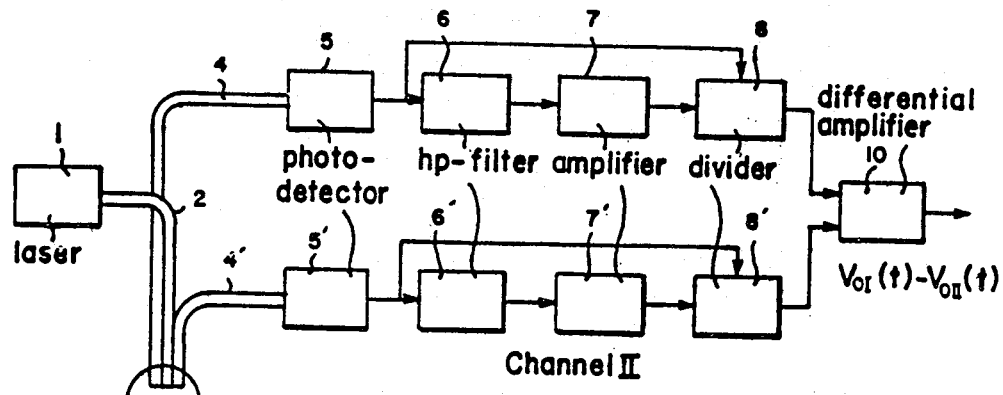
FIGS. 3 and 4 are a block diagram for an apparatus according to the invention.

In an apparatus according to the invention, as illustrated schematically and by way of example in FIG. 3, light from a laser 1 (e.g. a 5 mV He-Ne-laser of the type Spectral Physics Model 120), is transmitted through an optical plastic fibre 2 to the skin surface 3 to be investigated. Scattered spectral-broadened light from at least partially separated but mutually adjacent regions of the illuminated tissue area is gathered and transmitted to two separate photodetectors 5 and 5', respectively, through optical plastic fibres 4 and 4', respectively. The photodetectors may be of the type UDT-450 from United Detector Technology. The output signal of each detector 5 and 5', respectively, is processed in an associated signal processing channel I and II, respectively, in a similar manner as the output signal from the single photodetector 5 in the prior art apparatus according to FIG. 1. The high-pass filters 6 and 6' may have a cut-off frequency of 75 Hz (3 dB). The blood flow related output signals from the dividers 8 and 8' in channel I and channel 2, respectively, are connected to a differential amplifier 10. Since in the output signals from the dividers 8 and 8' in the channels I and II, respectively, the high-amplitude disturbances caused by mode interference in the laser beam are in phase with each other, these disturbances will be effectively suppressed in the output signal from the differential amplifier 10. For the same reason, also wide-band noise as well as disturbances caused by intensity variations in the laser beam and by external optical disturbance signals, such as 60 Hz intensity variations in the ambient light, will be effectively suppressed in the output signal from the differential amplifier 10. The blood flow related beat frequency components in the output signals from the two channels I and II will, on the contrary, be augmented and amplified in the differential amplifier 10, as these signal components are mutually statistically independent realisations of the same stochastic process, since they originate from different blood cells in the blood flow.

Figure 4:
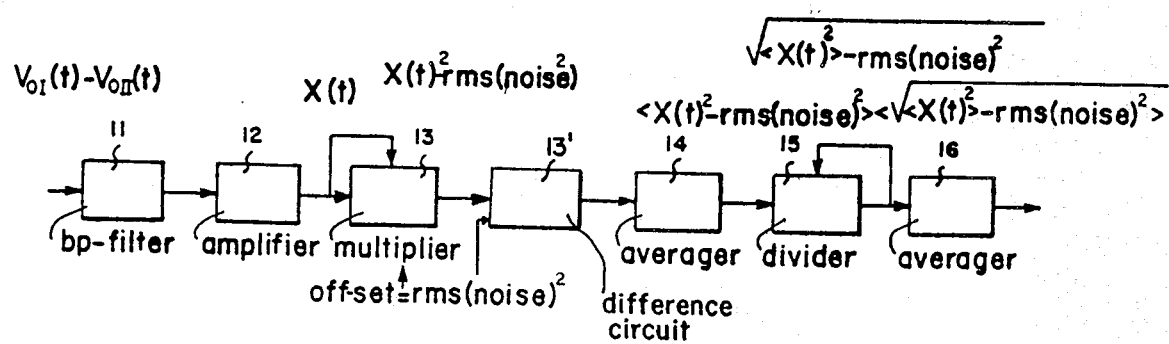

The output signal of the differential amplifier 10 is processed in the signal processing circuitry illustrated in FIG. 4 and the output signal from this signal processing circuitry is recorded in the diagram in FIG. 5 for an experiment similar to the one described in the foregoing with reference to the prior art apparatus according to FIG. 1 and the result of which is shown in FIG. 2.

As can be seen from the diagram in FIG. 5, the apparatus according to the invention provides a blood flow related output signal, in which high amplitude disturbances due to mode interference in the laser beam are removed and furthermore the wide-band beam amplitude noise has been rejected, so that the signal-to-noise ratio has been increased by a factor of 4.

In the signal processing circuitry shown in FIG. 4 the output signal from the differential amplifier 10 is supplied to a band-pass filter 11, which may have its cut-off frequencies e.g. at 4 kHz and 7 kHz (3 dB). The output signal from the filter is amplified in a linear amplifier 12 and squared in a multiplier 13. A difference circuit 13' receives the output from the multiplier 13 and a negative off-set signal corresponding to the signal value in the absence of any blood flow, i.e. corresponding to the square of the rms value of the noise. The signal is subsequently averaged in an averager 14 and its square-root is computed in an analog divider 15. The output signal from the divider 15 is finally averaged in an averager 16. The output of the averager 16 is a dc voltage equal to the rms value of the blood flow related signal alone. The time-constant of the output signal is set by the averager 16, and this time-constant can be varied in accordance with the desired response time of the measurement. The purpose of the difference circuit 13 is to cancel noise which is generated by the photodetectors 5,5' themselves, as distinguished from noise in the laser 1 and from external disturbances.

FIG. 6 shows schematically and by way of example a possible arrangement of the optical fibres in the end of the measuring probe, which is applied against the skin surface 2 to be examined. The central optical fibre 2 transmits light from the laser 1 towards the skin surface. Four afferent optical fibres are arranged in a circle surrounding the central optical fibre 2 with their end-surfaces lying in substantially the same plane as the light emitting end-surface of the central optical fibre 2. Two of these surrounding optical fibres 4 have their opposite ends optically coupled to the photodetector 5 of the channel I so as to transmit scattered light to this photodetector, whereas the two remaining afferent fibres 4' have their opposite ends optically coupled to the photodetector 5' of the channel II so as to transmit scattered light to this photodetector. It will be appreciated that also other configurations of the optical fibres in the measuring probe can be used. Thus, a larger number of afferent optical fibres transmitting scattered lights to the two photodetectors can be used. These afferent optical fibres can also have a smaller diameter than the central irradiating fibre 2.

FIG. 7 shows schematically, in section and at an enlarged scale, the distal end of the measuring probe and the upper layers of the skin comprising the epidermis and the corium. Red blood cells having an average diameter of about 7 μm move from the subdermal blood vessels up into the intricate capillary network of the skin, which is illuminated with light transmitted through the optical fibre 2. The effective radiation penetration depth is approximately 1 mm. The scattered light gathered by the afferent optical fibres 4 and 4', respectively, does not originate from two identical blood cells, but as the random movements of different blood cells are mutually statistically independent realisations of the same stochastic process, the signals in the channels I and II will both represent the blood flow in the capillary network.

We claim:

1. A method of determining flow motions in a fluid containing light scattering particles, such as for determining blood circulation in superficial blood vessels in a tissue, the method comprising the steps of illuminating the fluid with monochromatic light; gathering light scattered by the particles in in the fluid and any adjacent substantially stationary structures from two, at least partially separated but mutually adjacent regions of the illuminated section of the fluid; transmitting the light gathered from said two regions separately to two different photodetectors, these two photodetectors receiving light scattered at least partially from different particles; deriving from the respective output signal from each of the photodetectors a respective signal representing the beat frequency components between light components with different frequencies received by the respective photodetector; subtracting the two signals so derived from the output signals of the respective photodetectors from one another; and using the resulting signal from this signal subtraction as a measure of flow motions in the fluid.

2. A method as claimed in claim 1, wherein the output signals of each of the photodetectors are subjected to respective high-pass filtering and are subsequently normalized by being divided by the total output signal of the respective photodetector.

3. A method as claimed in claim 1, wherein the resulting signal from the signal substraction is subjected to a band-pass filtering and is subsequently squared.

4. A method as claimed in claim 3, wherein the band-pass filtered and squared signal has substracted therefrom a signal adjusted to correspond to the value of the band-pass filtered and squared signal in the absence of flow motions in the fluid and is subsequently averaged.

5. An apparatus for determining flow motions in a fluid containing light scattering particles, such as for determining blood circulation in superficial blood vessels of a tissue, the apparatus comprising a single monochromatic light source; means for illuminating the fluid with light from said single monochromatic light source; two photodetectors; means for gathering light scattered by particles in the fluid and any adjacent stationary structures separately from two, at least partially separated but mutually adjacent regions of an illuminated section of the fluid and for transmitting light gathered from said two regions separately to said two photodetectors; respective, separate signal processing circuitry for each of said photodectors coupled to respective outputs thereof and responsive to respective output signals therefrom for deriving from the output signals of the photodetectors signals containing beat frequency components originating from interference between light components of different frequencies received by respective photodetectors; and a signal subtracting circuit coupled to said respective signal processing circuitries for subtracting output signals from said two signal processing circuitries from one another.

6. An apparatus as claimed in claim 5, wherein each of said signal processing circuitries includes a respective high-pass filter.

7. An apparatus as claimed in claim 6, wherein each of said signal processing circuitries includes additionally, a respective signal dividing circuit for dividing a respective high-pass filtered signal from a respective one of said high-pass filters by the total output signal of a respective one of said photodetectors.

8. An apparatus as claimed in claim 5, including additional signal processing circuitry coupled to an output of said signal subtracting circuit and comprising a band-pass filter.

9. An apparatus as claimed in claim 7 or 8, wherein said means for illuminating the fluid comprises a first optical fibre having one end optically coupled to the light source and its opposite end movable for being directed towards a desired section of the fluid for the illumination thereof, and said means for gathering scattered light comprises at least two additional optical fibres having their one ends optically coupled to one photodetector each and their opposite ends movable together with said opposite end of said first optical fibre with their light gathering end-surfaces disposed adjacent to and substantially in the same plane as the light emitting end-surface of said first optical fibre.

10. An apparatus as claimed in claim 9, comprising a plurality of said additional optical fibres arranged with their light gathering end-surface in a circle around the light emitting end-surface of said first optical fibre, half the number of said additional optical fibres being jointly optically coupled to the one photodetector and the remaining additional optical fibres being jointly optically coupled to the second photodetector.

11. An apparatus as claimed in claim 5 or 6, wherein said means for illuminating the fluid comprises a first optical fibre having one end optically coupled to the light source and its opposite end movable for being directed towards a desired section of the fluid for the illumination thereof, and said means for gathering scattered light comprises at least two additional optical fibres having their one ends optically coupled to one photodetector each and their opposite ends movable together with said opposite end of said first optical fibre with their light gathering end-surfaces disposed adjacent to and substantially in the same plane as the light emitting end-surface of said first optical fibre.

12. An apparatus as claimed in claim 11, comprising a plurality of said additional optical fibres arranged with their light gathering end-surface in a circle around the light emitting end end-surface of said first optical fibre, half the number of said additional optical fibres being jointly optically coupled to the one photodetector and the remaining additional optical fibres being jointly optically coupled to the second photodetector.

* * * * *